(12) United States Patent
Ostrowski et al.

(10) Patent No.: US 7,915,032 B2
(45) Date of Patent: Mar. 29, 2011

(54) SAMPLE COLLECTION SYSTEM AND METHOD

(75) Inventors: Mark Ostrowski, Greenville, SC (US); Thomas Gerald Aucoin, Cary, NC (US)

(73) Assignees: Capitol Vial Inc., Auburn, AL (US); Laboratory Corporation of America Holdings, Burlington, NC (US)

( * ) Notice: Subject to any disclaimer, the term of this patent is extended or adjusted under 35 U.S.C. 154(b) by 1340 days.

(21) Appl. No.: 11/276,521

(22) Filed: Mar. 3, 2006

(65) Prior Publication Data

US 2007/0208274 A1 Sep. 6, 2007

(51) Int. Cl.
| C12M 1/34 | (2006.01) |
| C12M 3/00 | (2006.01) |
| B01L 99/00 | (2010.01) |
| B01L 3/00 | (2006.01) |
| B01L 3/02 | (2006.01) |

(52) U.S. Cl. ........... 435/287.7; 422/56; 422/58; 422/99; 422/102; 436/174; 436/176; 436/177; 436/178; 436/180; 435/309.1

(58) Field of Classification Search ............... 435/287.7, 435/4; 604/1, 2, 3
See application file for complete search history.

(56) References Cited

U.S. PATENT DOCUMENTS

| 3,776,220 | A |   | 12/1973 | Monaghan |
| 4,014,322 | A | * | 3/1977 | Shah ............................. 600/573 |
| 4,147,752 | A | * | 4/1979 | Suovaniemi et al. ........... 422/57 |
| 4,184,483 | A | * | 1/1980 | Greenspan .................... 600/572 |
| D256,053 | S |   | 7/1980 | Steigerwald |
| 4,278,437 | A |   | 7/1981 | Haggar |
| 4,653,510 | A |   | 3/1987 | Koll |
| 4,749,655 | A |   | 6/1988 | Monthony et al. |
| 4,774,962 | A |   | 10/1988 | Hebel et al. |
| 4,783,056 | A |   | 11/1988 | Abrams |
| 4,803,998 | A |   | 2/1989 | Kezes et al. |
| 4,812,116 | A |   | 3/1989 | Abrams |
| 4,877,036 | A |   | 10/1989 | Saint-Amand |
| 5,000,193 | A |   | 3/1991 | Heelis et al. |
| 5,091,316 | A |   | 2/1992 | Monthony et al. |
| 5,133,470 | A |   | 7/1992 | Abrams et al. |
| 5,151,094 | A |   | 9/1992 | Hanifl |
| 5,246,856 | A |   | 9/1993 | Gaarslev |
| 5,268,148 | A |   | 12/1993 | Seymour |
| 5,334,502 | A |   | 8/1994 | Sangha |
| 5,380,492 | A |   | 1/1995 | Seymour |

(Continued)

OTHER PUBLICATIONS

Sarstedt AG & CO., Salivette, Medical and Diagnostic Products [on line], 2003. Retrieved from internet: http://www.sarstedt.com/php/main.php?newlanguage=en (2 pages).

(Continued)

*Primary Examiner* — William H Beisner
*Assistant Examiner* — Danielle Henkel
(74) *Attorney, Agent, or Firm* — Wood, Herron & Evans, LLP (57) ABSTRACT

A sample collection system includes a vial and a collection stick. The collection stick includes an elongated handle portion and an absorbent head portion detachably connected to the handle portion. The absorbent head portion is configured to absorb and retain the fluid sample therein prior to insertion of the collection stick within the vial. During the sample collection process, the collection stick is inserted into the vial to express the fluid sample from the absorbent head portion into the vial. The absorbent head portion is retained within the vial in a generally compressed state with the handle portion being detached and removed from the vial.

26 Claims, 7 Drawing Sheets

U.S. PATENT DOCUMENTS

| | | |
|---|---|---|
| 5,393,496 A | 2/1995 | Seymour |
| 5,477,863 A | 12/1995 | Grant |
| 5,627,071 A | 5/1997 | Triva |
| 5,723,085 A | 3/1998 | Abrams et al. |
| 5,830,410 A | 11/1998 | Thieme et al. |
| 5,979,804 A | 11/1999 | Abrams et al. |
| 6,021,681 A | 2/2000 | Jezek |
| 6,176,836 B1 | 1/2001 | Trudil et al. |
| 6,245,037 B1 | 6/2001 | Reum et al. |
| 6,303,064 B1 | 10/2001 | Abrams et al. |
| RE37,676 E | 4/2002 | Abrams et al. |
| 6,398,067 B1 | 6/2002 | Belfance et al. |
| 6,406,451 B1 | 6/2002 | Rowe |
| 6,440,087 B1 | 8/2002 | Sangha |
| 6,489,172 B1 | 12/2002 | Bachand et al. |
| 6,514,224 B1 | 2/2003 | Anapliotis |
| 6,524,530 B1 | 2/2003 | Igarashi et al. |
| 6,531,096 B1 | 3/2003 | Deveney et al. |
| 6,592,280 B2 | 7/2003 | Petrich et al. |
| D483,496 S | 12/2003 | Kjendlie |
| 6,705,463 B1 | 3/2004 | Bucholtz et al. |
| 6,740,049 B2 | 5/2004 | Wallach |
| 6,769,558 B1 | 8/2004 | Bucholtz |
| D507,351 S | 7/2005 | Birnboim |
| 6,921,395 B2 | 7/2005 | Carano et al. |
| 7,282,181 B2 * | 10/2007 | Hudak et al. .................. 422/99 |
| 2001/0039058 A1 | 11/2001 | Iheme et al. |
| 2002/0136665 A1 | 9/2002 | Hayton et al. |
| 2002/0197738 A1 | 12/2002 | Matsumoto et al. |
| 2004/0158188 A1 | 8/2004 | Kauffmann et al. |
| 2004/0170536 A1 | 9/2004 | Daykin |
| 2004/0267181 A1 | 12/2004 | Tuite et al. |
| 2005/0010132 A1 | 1/2005 | Pestes et al. |
| 2005/0010133 A1 | 1/2005 | Pestes et al. |
| 2005/0136553 A1 | 6/2005 | Kaylor et al. |
| 2005/0252820 A1 * | 11/2005 | Sanchez-Felix et al. ..... 206/569 |
| 2006/0057027 A1 | 3/2006 | Hudak et al. |
| 2009/0202393 A1 * | 8/2009 | Gallagher et al. ............ 422/102 |
| 2009/0209044 A1 * | 8/2009 | Gallagher et al. ............ 436/174 |

OTHER PUBLICATIONS

United States Patent and Trademark Office, Non-Final Office Action, U.S. Appl. No. 12/364,831, mailed Mar. 30, 2010 (21 pages).

United States Patent and Trademark Office, Non-Final Office Action, U.S. Appl. No. 12/030,600, mailed Apr. 2, 2010 (20 pages).

* cited by examiner

SAMPLE COLLECTION SYSTEM AND METHOD

FIELD OF THE INVENTION

The present invention relates generally to sample collection systems and, more particularly, to a sample collection system for collecting and transporting a fluid sample.

BACKGROUND OF THE INVENTION

Fluid samples are often collected for diagnostics testing including, by way of example, "drugs of abuse" testing, hormone replacement therapy, other diagnostics and clinical testing including HIV screening, environmental sampling, veterinarian sample collection and other similar applications. The substances collected are varied and include, for example, bodily fluids such as saliva, blood, urine, surface moisture from any type of surface including exterior body surfaces, or any other type of fluid that is typically subjected to diagnostics testing.

It is a common practice to use a swab of absorbent material as a collection medium. The swab is often mounted on an end of a collection stick and is supplied in a kit that also contains a container or vial into which the swab and sample are placed for purposes of transportation or analysis. The vial may contain a buffer solution into which the swab with the sample is submerged.

To collect a sample, the swab is brought into contact with the fluid sample to be collected to transfer the sample to the swab. The swab is then placed in the vial and submerged in the buffer solution. There are many variations in the subsequent sample collecting process depending on how the collected sample is to be analyzed. For example, in some applications, the sample is analyzed contemporaneously with it being collected, and that process may be carried out in the vial or a contiguous container. However, in other applications, the vial with the collected sample is sealed and sent to a different location for subsequent analysis.

With known sample collection systems in which a collected sample is to be shipped to a location for analysis, it is known to seal the swab and the collection stick in the vial for transportation to the location of analysis. At the location of analysis, a technician typically uses the collection stick to compress the swab against the bottom of the vial to extract or express the sample from the absorbent swab into the buffer solution. The swab is then removed from the vial and may be discarded. A pipette or other instrument is then introduced into the vial to remove a mixture of the fluid sample and buffer solution from the vial for analysis.

However, it will be appreciated that if the swab is not sufficiently compressed in the vial by the technician to express the sample from the swab, the integrity of the analysis may be compromised. Moreover, requiring the technician performing the analysis to extract the sample from the swab generally increases the cost and complexity of the analysis process and also risks contamination of the sample while the collection stick is being handled.

Therefore, there is a need for a sample collection system that simplifies the extraction of a fluid sample from a collection stick for subsequent analysis of the sample. There is also a need for a sample collection system that assures proper mixing of a fluid sample and buffer solution within a vial for accurate analysis of the sample.

SUMMARY OF THE INVENTION

The present invention overcomes the foregoing and other shortcomings and drawbacks of sample collection systems heretofore known for use in collecting and transporting fluid samples for analysis. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, a sample collection system is provided including a vial and a collection stick. The vial has a wall defining a closed end and an open end and may be configured to contain an optional buffer solution within the vial. A cap is provided to selectively seal with the open end of the vial.

In one embodiment, the collection stick has an elongated handle portion and an absorbent head portion detachably connected to the handle portion. The absorbent head portion is configured to absorb and retain the fluid sample within the absorbent head portion prior to insertion of the collection stick within the vial.

According to one aspect of the present invention, the vial wall and the absorbent head portion are configured to permit insertion of the collection stick into the vial so that the absorbent head portion is compressed against the closed end of the vial to express the fluid sample from the absorbent head portion and mix with a buffer solution within the vial if the buffer solution is present within the vial. The elongated handle portion is detached from the absorbent head portion and removed from the vial while the absorbent head portion is retained in a generally compressed state within the vial.

According to another aspect of the present invention, the sample collection system provides an audible and/or tactile indication to a user to indicate that the collection stick has been sufficiently inserted into the vial to express the fluid sample from the absorbent material. Following receipt of this audible and/or tactile indication, the user detaches the handle portion from absorbent head portion and removes the handle portion from the vial prior to sealing the vial with the cap.

The present invention provides a sample collection system that simplifies the sample collection and extraction process and has several advantages over known processes for collecting and transporting a fluid sample for analysis. With the sample collection system of the present invention, a person collecting the fluid sample also extracts or expresses the collected sample from the absorbent material at the collection site. The sample collection system of the present invention permits the person collecting the sample to easily remove substantially all of the collection stick from the vial so that only the absorbent head portion and the collected fluid sample, or a mixture of the fluid sample a buffer solution, remain in the vial during transportation. This reduces a risk of contamination of the sample and allows the fluid sample or, alternatively, a mixture of the sample and buffer solution, to be readily removed from the vial using a pipette or other instrument. Thus, the sample collection system of the present invention improves the quality and reliability of a sample collecting procedure. The sample collection system of the present invention has further benefits in being structurally uncomplicated, easy to use and less labor intensive than known systems, thereby substantially increasing the efficiency and economy of the collection and analytical processes.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Figure 1:
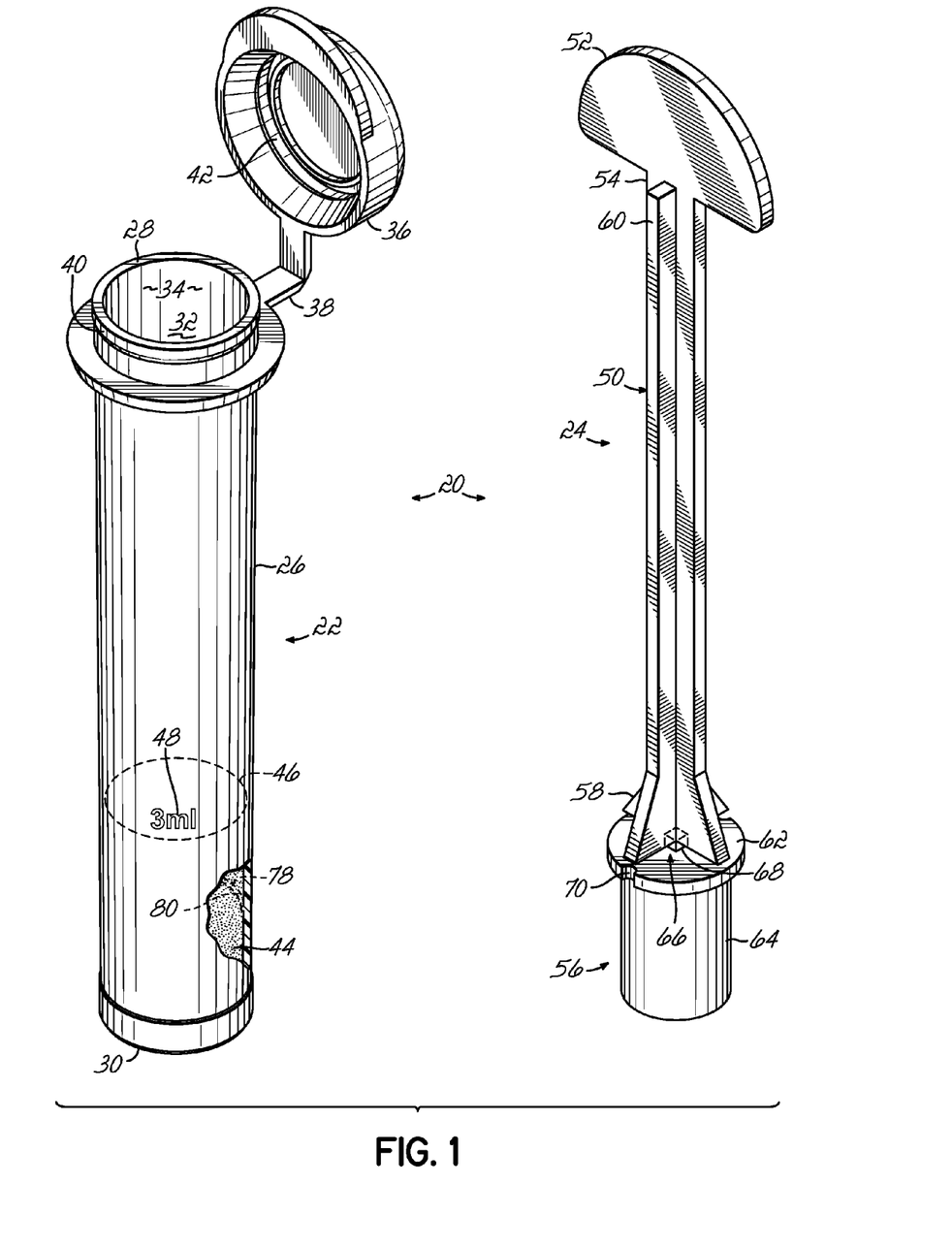
FIG. 1 is a perspective view of an exemplary embodiment of a vial and a collection stick used in a sample collection system in accordance with the principles of the present invention.

Referring now to the figures, and to FIG. 1 in particular, a collection kit or system 20 is shown in accordance with one embodiment of the present invention including a vial 22 and a collection stick 24 for collecting and transporting a fluid sample for diagnostics testing. By way of example, the fluid sample may comprise saliva, blood, urine, surface moisture from any type of surface including an exterior body surface, or any other type of fluid that is typically subjected to diagnostics testing. For example, the collection kit 20 can be used in applications such as "drugs of abuse" testing, hormone replacement therapy, other diagnostics and clinical testing including HIV screening, environmental sampling, veterinarian sample collection and other similar applications.

The vial 22 has a vial wall 26 that defines an open end 28, a closed end 30, and an interior surface 32 extending between the open and closed ends 28, 30 of the vial to form a vial cavity 34. In one embodiment, a cap 36 is connected to the vial 22 by means of a flexible hinge strap or tab 38. The open vial end 28 has an annular sealing flange 40 that is engageable with an annular groove 42 in the cap 36 to seal the open end 28 of the vial 22 during transportation of the vial to and from the collection site as will be described in greater detail below. The vial 22, cap 36 and strap or tab 38 may be made of plastic or other suitable material and may be integrally molded as a single component during a molding operation as will be understood by those of ordinary skill in the art. For example, the vial 22, cap 36 and strap or tab 38 may be made of polypropylene, polyethylene, polystyrene or any other suitable FDA approved material.

One example of a suitable molding process, which example is not meant to be limiting, is a conventional injection molding process that is disclosed in U.S. Pat. No. RE 37,676 (the entire disclosure of which is incorporated herein by reference). More particularly, as discussed in this patent, molten plastic may be injected through a sprue gate with about fifteen tons of pressure so as to form the product (at the same time, a press may be used to apply about fifteen tons of pressure to a mold). The injected product may be allowed to cool for about six seconds while the temperature thereof drops from about 550° F. to about 100°-120° F. The specific temperature to which the product is formed and the time, prior to opening the mold, may be dependent on numerous factors including the type of plastic, and size and type of product but should be cool enough so that the plastic will retain its shape, and hot enough so that the plastic is not fully set. Water may be circulated through water channels in the mold in order to accelerate the cooling of the product.

In another embodiment, the product may be ejected from the mold using any conventional design known in the art that completely removes the product from the mold without incurring damage thereto. For example, a jet of air may drive an air poppet through its housing until it contacts the product and pushes it from the mold. When the air poppet is projected into the mold cavity, air currents that drive the air poppet may further assist in ejecting the product. The air poppet may be provided with an angled surface that will contact the product in a flat manner so as not to mark the product. In another example, a mechanical pusher may be employed to contact the product and push it out of the mold. In a further example, an ejector sleeve may be employed to push the product out of the mold. In a still further example, a robot mechanism may be employed to remove the product. Additional plastic may then be injected into the mold to repeat the cycle.

Other patents disclosing a mold/molding process, which examples are not meant to be limiting, include U.S. Pat. No. 4,783,056, U.S. Pat. No. 4,812,116 and U.S. Pat. No. 6,303,064 (the entire disclosure of each patent relating to the process of molding of vials is incorporated herein by reference).

In one embodiment, the vial 22 is partially filled with a buffer solution 44 up to the level of a fill line 46 and the cap 36 is thereafter engaged over the vial open end 28 to seal the vial 22 prior to use of the collection kit 20. The optional fill line 46 may be printed, molded or otherwise marked or formed on the vial wall 26 to indicate the desired level of buffer solution 44 within the vial 22. Numerical indicia 48 may be provided on the vial wall 26 to indicate the volume of buffer solution 44 contained within the vial 22. The vial 22 may be made of a sufficiently translucent material so that the level of buffer solution 44 within the vial 22 may be readily observed through the vial wall 26. Alternatively, the vial 22 may be generally opaque and/or made of a resin providing ultraviolet (UV) protection to prevent change to the fluid sample within the vial 22 due to light exposure.

In one embodiment, the collection stick 24 has an elongated handle portion 50 including a handle 52 at one end 54 and an absorbent head portion 56 detachably connected to the opposite end 58 of the handle portion 50. The handle 52 is designed to be easily grasped by a user to facilitate collection of the fluid sample and insertion of the collection stick 24 into the vial 22. The handle portion 50 includes a plurality of longitudinally extending ribs 60 that add rigidity to the collection stick 24. The ribs 60 flare outwardly near the end 58 of the handle portion 50 to maintain the orientation of the absorbent head portion 56 while the collection stick 24 is inserted within the vial cavity 34 toward the closed end 30 of the vial 22. As will be described in greater detail below, the absorbent head portion 56 is configured to contact a fluid, such as saliva from a donor's mouth, and absorb and retain the fluid sample within the absorbent head portion prior to insertion of the collection stick 24 within the vial 22.

In one aspect of the invention, the absorbent head portion 56 includes a support member 62 that is detachably connected to the end 58 of the handle portion 50 and a wad, swab or plug of absorbent material 64 supported by and below the support member 62. In one embodiment, a frangible member 66, such as a pin 68, is connected between the support member 62 and the end 58 of the handle portion 50. The pin 68 is configured to break or separate upon twisting of the handle portion 50 relative to the support member 62 so as to permit detachment of the handle portion 50 from the absorbent head portion 56 after the collection stick 24 has been sufficiently inserted into the vial 22 to mix the collected fluid sample with the buffer solution 44 as will be described in detail below. The absorbent head portion 56 remains in the vial 22 following detachment and removal of the handle portion 50. The handle portion 50, support member 62 and frangible member 66 may be made of plastic or other suitable material and integrally molded as a single component during a molding operation as will be understood by those of ordinary skill in the art. For example, the collection stick 24 may be made of polypropylene, polyethylene, polystyrene or any other suitable FDA approved material.

Alternatively, the handle portion 50 and the support member 62 may be manufactured separately and then connected together through a detachable connection. For example, a mechanical interlock (not shown) may be provided between the end 58 of the handle portion 50 and the support member 62 so that the handle portion 50 is detachably connected to the absorbent head portion 56. Accordingly, it will be appreciated that other methods of detachably connecting the handle portion 50 to the absorbent head portion 56 are possible as well without departing from the spirit and scope of the present invention.

The absorbent material 64 may be operatively connected to the support member 62 by hot melt adhesive, tape, glue, a mechanical interlock or any other suitable connection method known to those of ordinary skill in the art. In one embodiment, the support member 62 has a generally disk shape although other shapes suitable for supporting the absorbent material 64 are possible as well without departing from the spirit and scope of the present invention. Alternatively, it will be appreciated that the support member 62 and the absorbent material 64 may be integrally formed as a single component without departing from the spirit and scope of the present invention.

According to another aspect of the present invention, the vial 22 has an inner diameter that decreases in a direction from the open end 28 to the closed end 30 so that the vial 22 has a gentle taper angle at least partially along its length. In one embodiment, the taper angle is generally uniform from generally proximate the open end 28 to generally proximate the closed end 30. The support member 62 has a diameter that is greater than the inner diameter of the vial 22 generally proximate the closed end 30 so that the support member 62 frictionally engages the interior surface 32 of the vial 22 generally proximate the closed end 30 when the collection stick 24 has been sufficiently inserted into the vial 22 to express the fluid sample from the absorbent material 64 as described in detail below.

The sealed and sterilized vial 22 and sterilized collection stick 24 are often packaged together in kit form for distribution and use. In one exemplary application of obtaining a sample of saliva using the collection stick 24, the absorbent material 64 is placed in a donor's mouth for a time sufficient for the absorbent material 64 to absorb or collect a sample of the saliva. Such absorption often occurs over a duration of about 2-5 minutes.

Figure 2A:
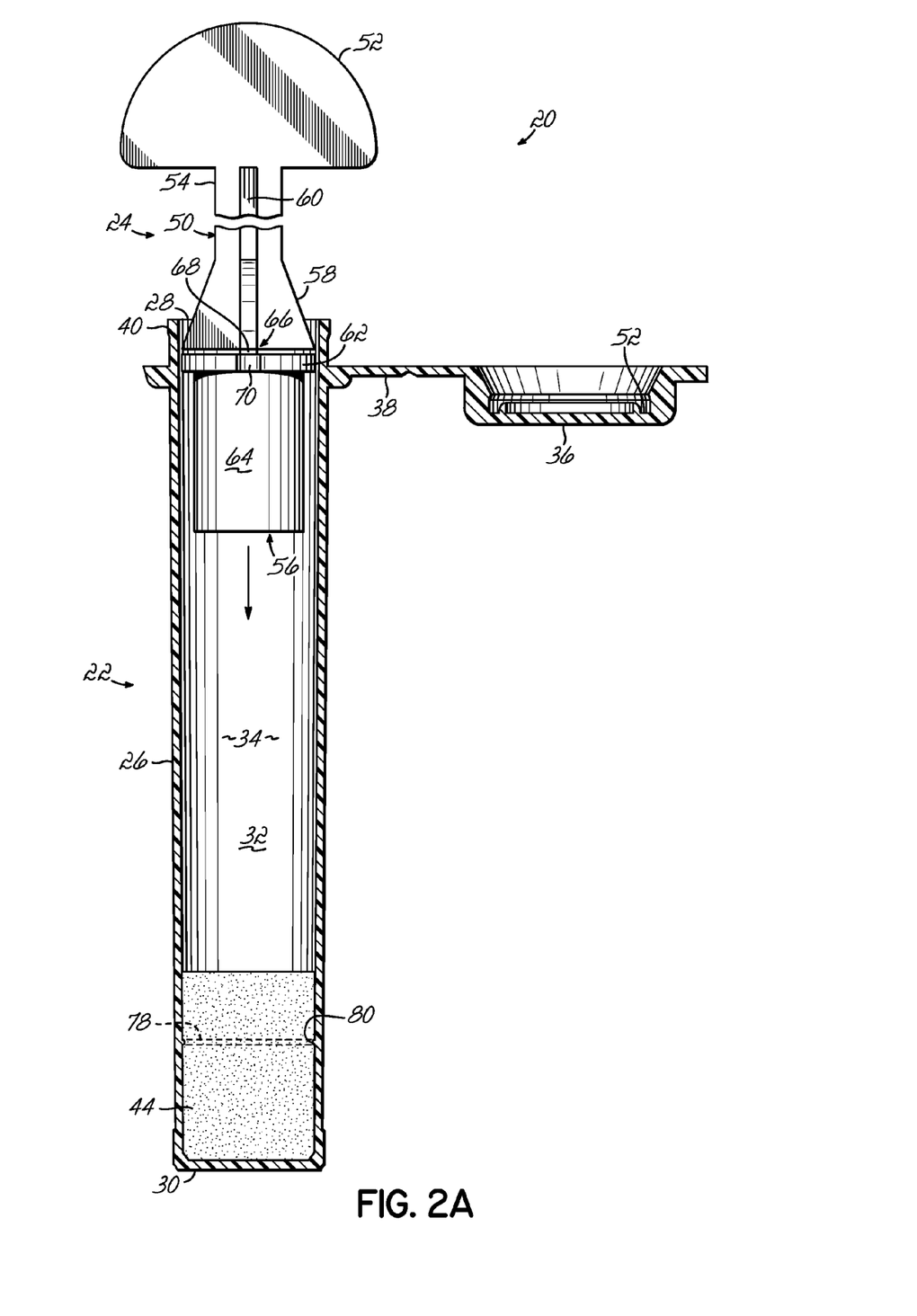
FIGS. 2A-2E are partial cross-sectional views illustrating various steps of using the collection stick and vial of FIG. 1 in collecting a sample and making it available for analysis.
Figure 2B:
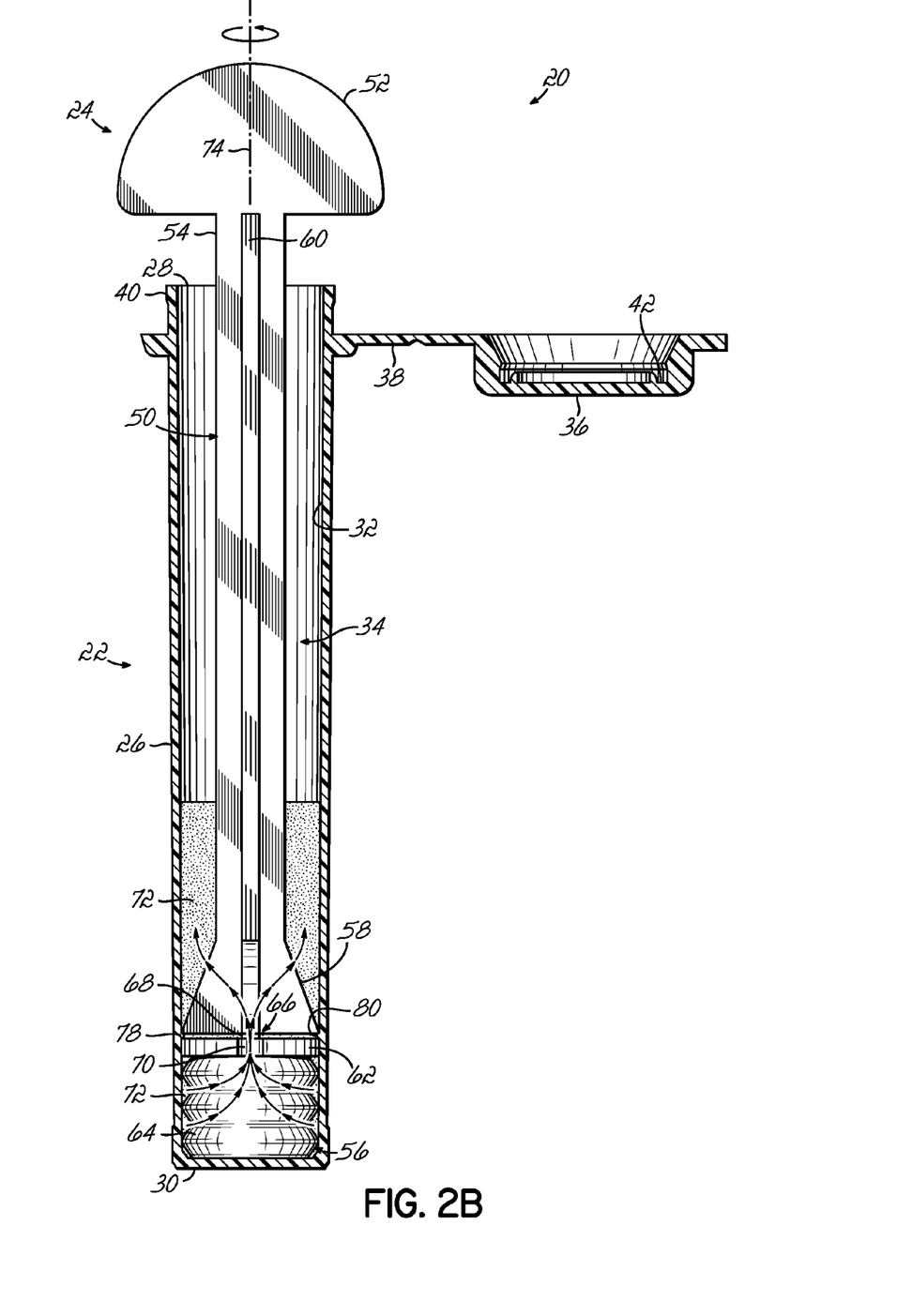

Next, as shown in FIG. 2A, the collection stick 24 is inserted through the vial open end 28 and urged within the vial cavity 34 toward the closed end 30. As the absorbent head portion 56 approaches the closed end 30 of the vial 22, the absorbent material 64 is submerged in the buffer solution 44 and contacts the closed end 30. As the user continues to urge the absorbent head portion 56 toward the closed end 30 via the handle portion 44 of the collection stick 24, the absorbent material 64 is compressed against the closed end 30 of the vial 22 as shown in FIG. 2B. The compression of the absorbent material 64 against the closed end 30 of the vial 22 causes the saliva sample to express from the absorbent material 64 and mix with the buffer solution 44. At the position shown in FIG. 2B, the support member 62 is frictionally engaged with the interior surface 32 of the vial 22 and the absorbent material 64 is in a generally compressed state.

Figure 3A:
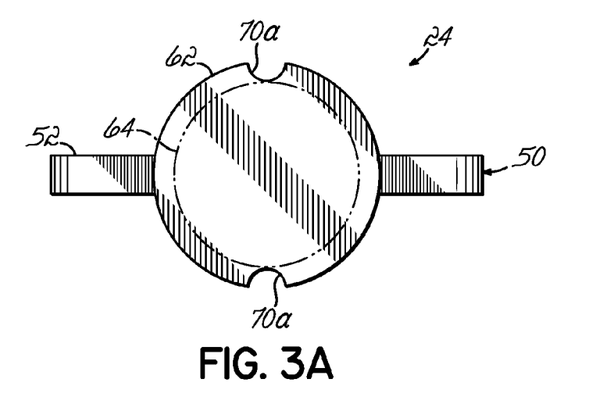
FIGS. 3A-3C are end views of a support member of the collection stick of FIG. 1 and illustrate different exemplary embodiments of openings provided in the support member.
Figure 3B:
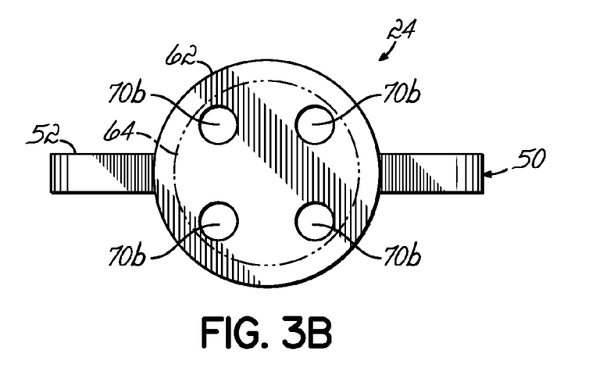
Figure 3C:
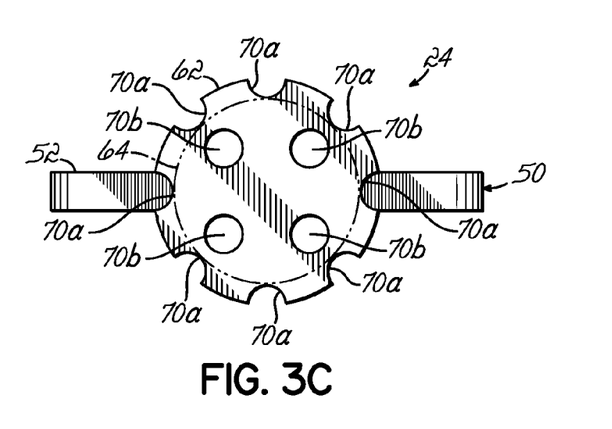

The support member 62 has one or more openings 70 that allow a mixture 72 of the fluid sample and the buffer solution to migrate from the bottom side of the support member 62 (i.e., the space between the closed end 30 of the vial 22 and the support member 62) to the opposite upper side as shown in FIG. 2B. For example, as shown FIG. 3A, two peripheral cutouts or slots 70a may be formed in the support member 62. Alternatively, as shown in FIG. 3B, through holes 70b extending through the support member 62 may be employed. In another embodiment, as shown in FIG. 3C, a combination of peripheral cutouts 70a and through holes 70b may be formed in the support member 62. It will be appreciated that other configurations of openings 70 are possible as well without departing from the spirit and scope of the present invention.

Following compression of the absorbent head portion 56 with the closed end 30 of the vial 22 as shown in FIG. 2B, the handle portion 50 is then twisted approximately 180° in either direction to rotate the handle portion 50 about an axial centerline 74. The support member 62 is prevented from rotating with the handle portion 50 due to its frictional engagement with the vial wall 26. The twisting force applied to the handle portion 50 causes the frangible pin 68 to break and thus separate the handle portion 50 from the absorbent head portion 56.

Figure 2C:
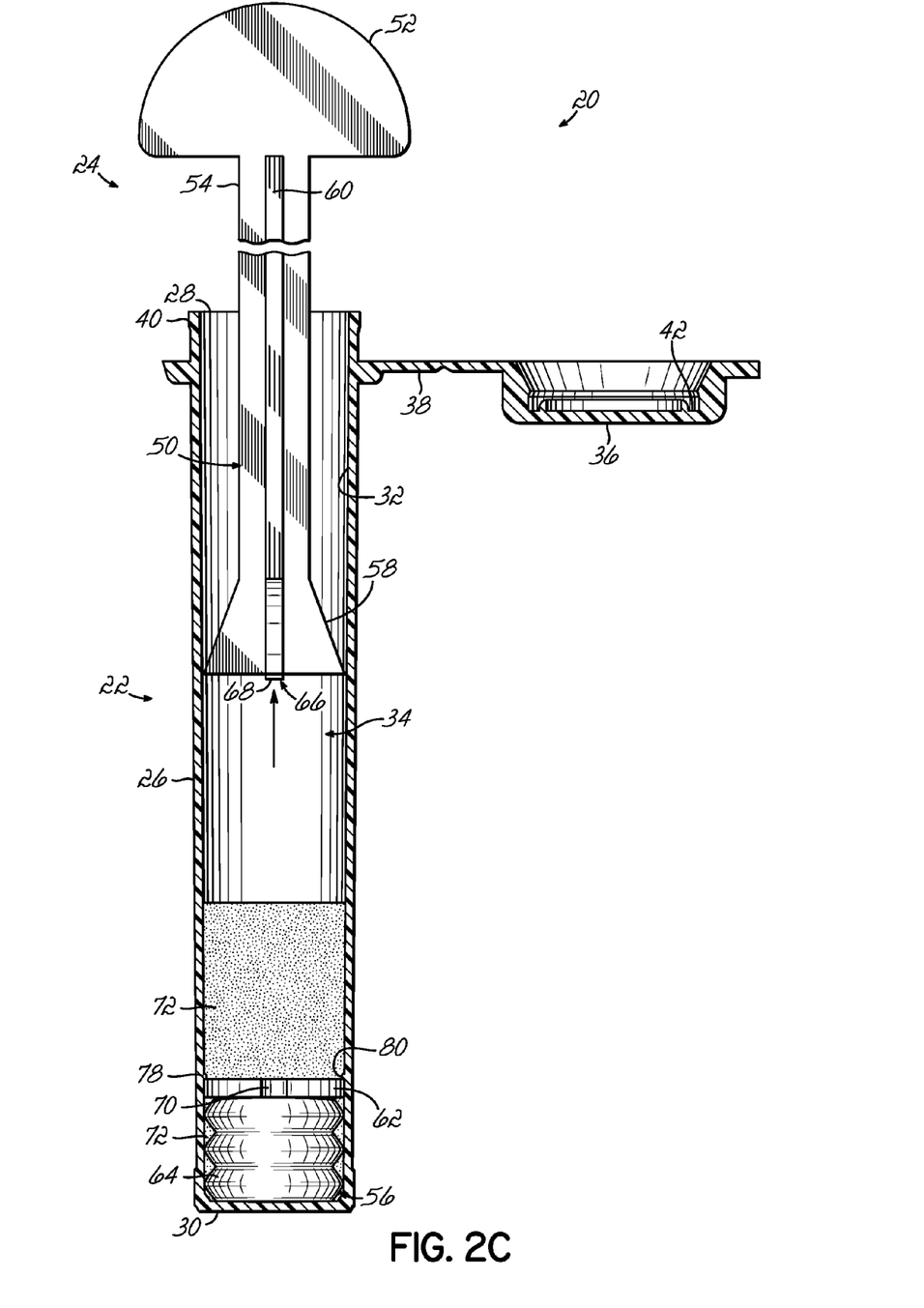

As shown in FIG. 2C, the handle portion 50 is then removed from the vial 22 and may be discarded. The absorbent head portion 56 is retained within the vial 22 with the absorbent material 64 in a generally compressed state. The mixture 72 of the fluid sample and the buffer solution is present in the vial 22 above the support member 62.

Figure 2D:
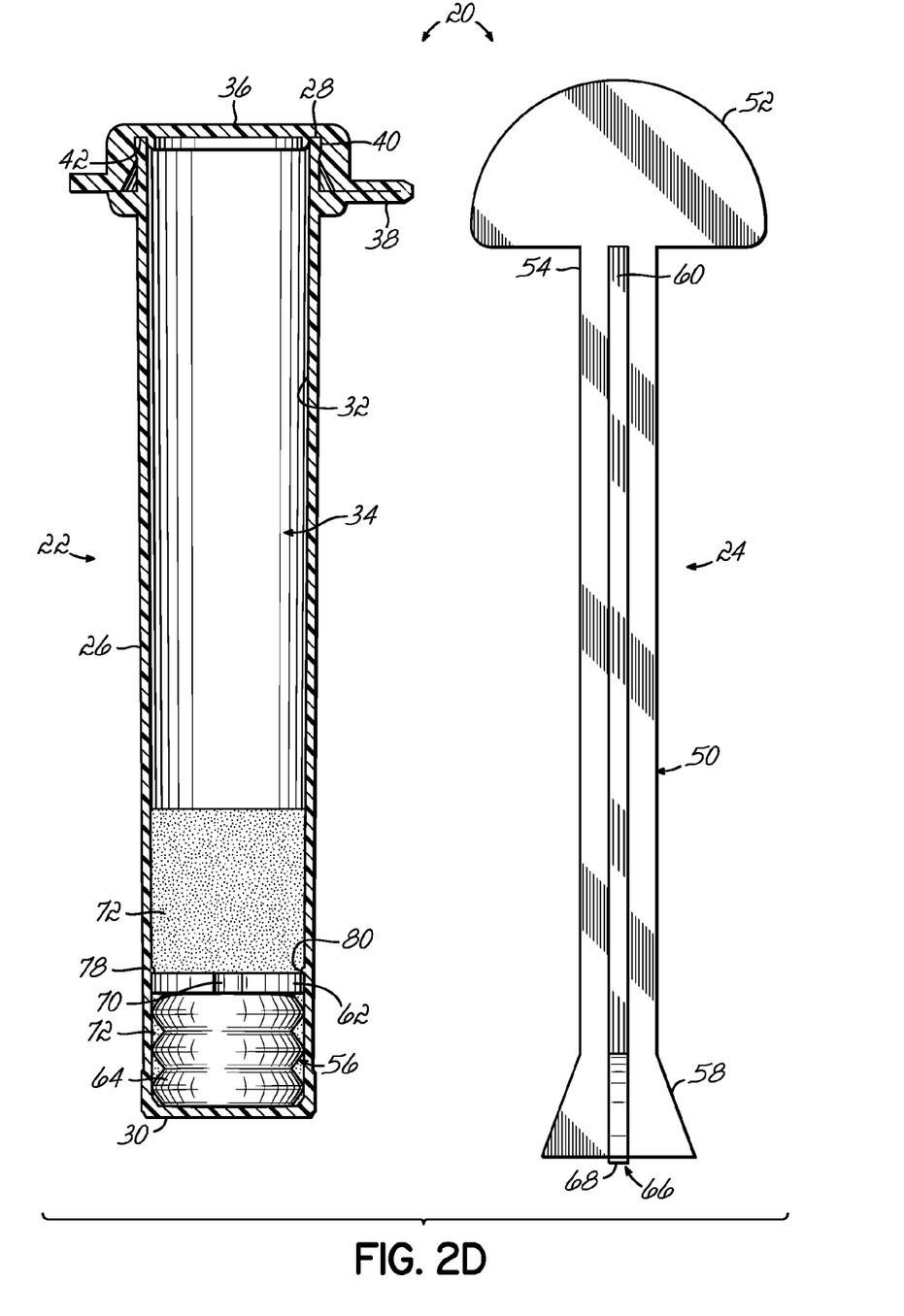
Figure 2E:
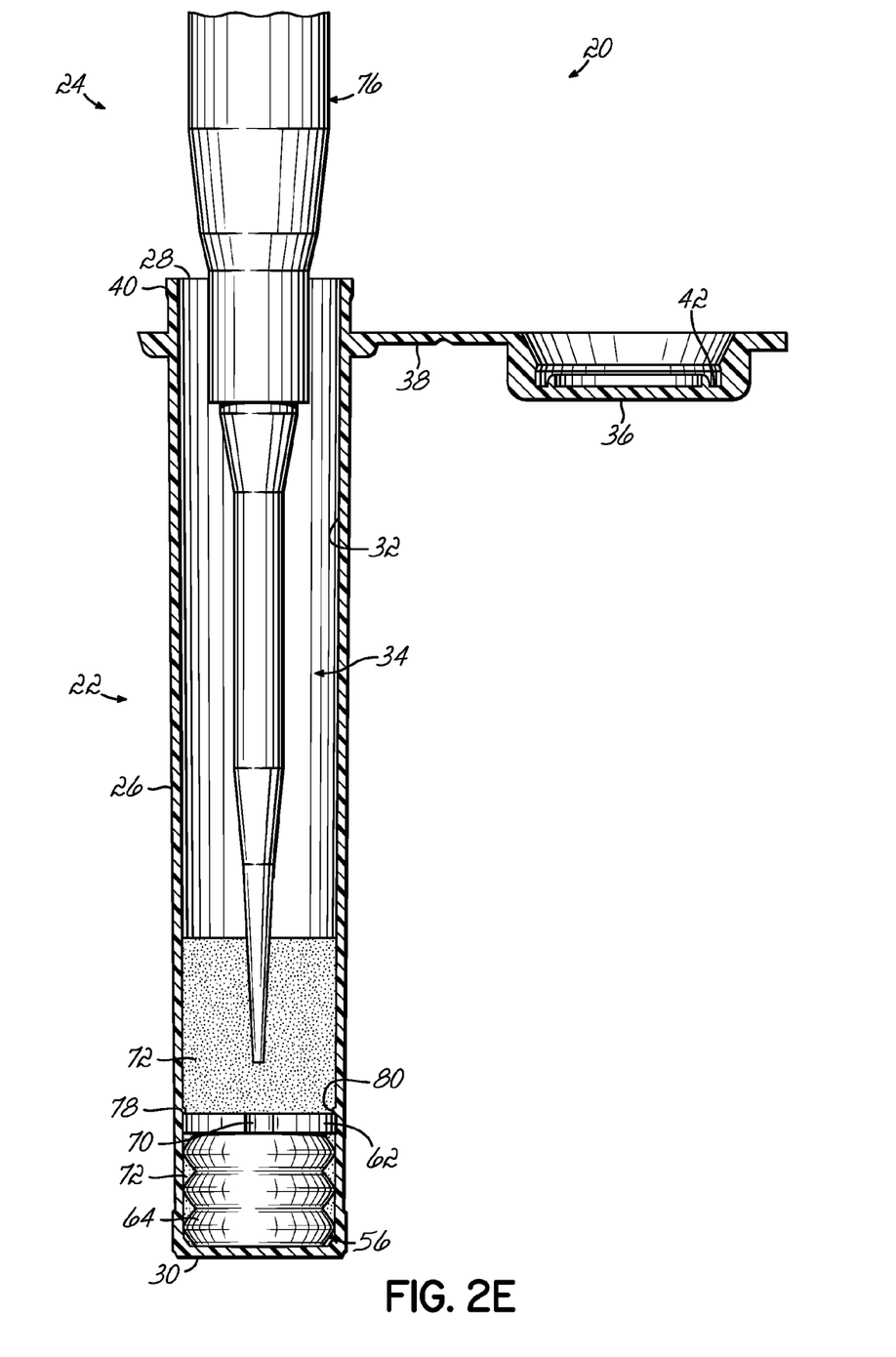

Thereafter, as shown in FIG. 2D, the cap 36 is sealingly engaged with the vial 22 and the vial with the mixture 72 of the fluid sample and buffer solution is then transported to a location where an analysis of the saliva sample is to be performed. As shown in FIG. 2E, the cap 36 is removed from the vial 22 at that location and a pipette 76 can be inserted into the vial 22 to collect the mixture 72 of the fluid sample and buffer solution for analysis.

It will be appreciated that other types of mechanical interferences known to those of ordinary skill in the art are possible as well to retain the absorbent head portion 56 within the vial 22 while permitting detachment of the handle portion 50 without departing from the spirit and scope of the present invention.

According to another aspect of the present invention, and as shown in FIGS. 2A-2E, a projection 78 is provided spaced from the closed end 30 of the vial 22 and extending inwardly from the interior surface 32 of the vial wall 26. In one embodiment, the projection 78 comprises a continuous annular rib 80 having a uniform radius that defines an inner diameter at the rib 80 that is slightly smaller than the diameter of the support member 62. As the absorbent head portion 56 is urged toward the closed end 30 of the vial 22 to compress the absorbent material 64, the support member 62 engages and rides over the rib 80. As this occurs, an audible "click" and/or a tactile indication is provided to the user to indicate that the collection stick 24 has been sufficiently inserted into the vial 22 to express the fluid sample from the absorbent head portion 56. Following receipt of this audible and/or tactile indication, the user then twists and removes the handle portion 50 and the absorbent head portion 56 is retained in the vial 22 in a generally compressed state. It will be appreciated that other configurations of projections capable of providing an audible and/or tactile indication to a user are possible as well without departing from the spirit and scope of the present invention.

In one exemplary embodiment of the present invention, the vial 22 may have a length of about 3.20 in. (8.12 cm) between the open and closed ends 28, 30 of the vial. The open end 28 of the vial may have an inner diameter of about 0.535 in. (1.35 cm) and the closed end 30 may have an inner diameter of about 0.490 in. (1.24 cm). The fill line 46 may be located about 1.075 in. (2.73 cm) above the closed end 30 of the vial 22 and the numerical indicia "3 ml" may be provided on the vial wall 26 adjacent the fill line 46. The annular rib 80 may be located about 0.480 in. (1.21 cm) above the closed end 30 of the vial 22 and have an axial height of about 0.020 in. (0.05 cm) and a radially inward depth of about 0.005 in. (0.01 cm) from the interior surface 32 of the vial wall 26. The annular rib 80 may define an inner diameter of about 0.486 in. (1.23 cm) at the rib.

The collection stick 24 may have length of about 3.675 in. (9.33 cm) excluding the absorbent material 64. The absorbent material 64 may have a length of about 0.562 in. (1.42 cm). The support member 62 may have a thickness of about 0.075 in. (0.19 cm) and a diameter of about 0.500 in. (1.27 cm). The frangible pin 68 may have a length of about 0.025 in. (0.06 cm). It will be appreciated that other dimensions and configurations of the vial 22 and collection stick 24 are possible as well without departing from the spirit and scope of the present invention.

The sample collection kit 20 of the present invention provides several advantages over known sample collection systems. For example, with the sample collection system 20 of the present invention, a person collecting the sample also performs the step of extracting the collected fluid sample from the absorbent material 64 into the buffer solution 44 at the collection site. During the extraction process, the handle portion 50 is used to compress the absorbent material 64 against the closed end 30 of the vial 22, thereby extracting the collected fluid sample and mixing it with the buffer solution 44. As part of the extraction process, the absorbent material 64 is automatically captured generally proximate the closed end 30 of the vial 22.

With the fluid sample extracted after collection but prior to analysis, the analytical process is simplified. The sample collection system 20 of the present invention permits the person collecting the sample to easily remove the handle portion 50 so that only the absorbent head portion 56 and the mixture 72 remain in the vial 22 during transportation. Removal of the handle portion 50 at the collection site reduces a potential for contamination of the sample and the mixture 72 is readily accessible at the analysis site for removal from the vial 22 using a pipette or other instrument.

Additionally, the audible and/or tactile indication provided by cooperation of the projection 78 with the support member 62 assures a user that the fluid sample has been sufficiently expressed from the absorbent head portion 56 and mixed with the buffer solution prior to analysis. Thus, the sample collection system improves the quality and reliability of the sample collecting procedure. The sample collection system 20 of the present invention has further benefits in being structurally uncomplicated, easy to use and less labor intensive than known systems, thereby substantially increasing the efficiency and economy of the collection and analytical processes.

The sample collection kit 20 may be used for collecting many different types of fluid samples and therefore, the absorbent material 64 and the buffer solution 44 may vary depending on the needs and requirements of a particular application. For example, while the absorbent material 64 is shown as being generally cylindrical in shape, in other embodiments, it may be hemispherical, straight-sided, fabricated from folded or layered material, etc. Thus, the size and/or shape of the absorbent material 64 is selected based on the diagnostics testing requirements. For example, for collecting a saliva sample, the absorbent material 64 may be a hydrophilic absorbent and selected so as to absorb and release fluids into the buffer solution for testing. In different embodiments, the hydrophilic absorbent may

- include extruded plastic material with a hollow cell configuration, or
- be a material interacting with a buffer solution and/or fluid to be tested, or
- be selected based in part on the desired interference between the absorbent and a fluid, or
- be a material for preventing tetrahydrocannabinol (THC) from binding with the absorbent, or
- include a polyurethane fiber material treated with a surfactant for providing a wicking action, wherein a degree of wicking is based on the amount of saliva or other fluid to be collected for testing purposes, or
- be a material made from at least one of a cotton fiber, a paperboard, plastic or other absorbent material.

The type and/or amount of the buffer solution 44 is selected to interact with a fluid, for example, saliva, to be tested. Typically, the buffer solution resists changes in pH when small quantities of an acid or alkali are added to it. An acid is a compound that donates a hydrogen ion to another compound whereas an alkali is a compound that accepts a hydrogen ion. Thus, generally, there are two types of buffer solutions: an acidic buffer solution having a pH less than 7 and an alkaline buffer solution with a pH greater than 7.

In one embodiment, an acidic buffer solution is a solution for resisting changes in pH, for example, a solution that is made from a weak acid and a corresponding salt, for example, sodium salt. In alternative embodiments, an acidic solution includes a mixture of ethanoic acid and sodium ethanoate. An acidic buffer solution containing equal molar concentrations of both the acid and the salt has a pH of approximately 4.76. The buffer solution can be changed by changing the ratio of acid to salt, or by choosing a different acid and one of its salts.

In another embodiment, an alkaline buffer solution is a solution for resisting changes in pH, for example, a solution that is made from a weak base and a corresponding salt. An alkaline solution may include a mixture of an ammonia solution and ammonium chloride solution. In this embodiment, an alkaline buffer solution having equal molar proportions of this base and acid has a pH of approximately 9.25. In acidic and alkaline solutions, the concentration of the mixture is independent of the amount of mixture as long as the concentration is the same.

In an alternative embodiment of the present invention, a buffer solution is not contained within the vial 22 when the fluid sample is introduced into the vial 22. In this alternative embodiment, the collection stick 24 is used to collect a fluid sample using the absorbent head portion 56 as described in detail above. The collection stick 24 is inserted through the open end 28 of the vial 22 and urged within the vial cavity 34 toward the closed end 30. As the user continues to urge the absorbent head portion 56 toward the closed end 30 via the handle portion 44 of the collection stick 24, the absorbent material 64 is compressed against the closed end 30 of the vial 22. The compression of the absorbent material 64 against the closed end 30 of the vial 22 causes the fluid sample to express from the absorbent material 64 and flow through the openings 70 into the vial cavity 34 where it can be later analyzed at the analysis site. The absorbent head portion 56 is retained within the vial 22 with the absorbent material 64 in a generally compressed state as described in detail above.

While the present invention has been illustrated by description of various embodiments and while those embodiments have been described in considerable detail, it is not the intention of applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of applicants' invention.

What is claimed is:

1. An apparatus for collecting a fluid sample, comprising:
a vial having a wall defining a closed end and an open end;
a cap configured to selectively seal with the open end of the vial; and
a collection stick having an elongated handle portion and an absorbent head portion detachably connected to the handle portion, the absorbent head portion being configured to absorb and retain the fluid sample therein prior to insertion of the collection stick within the vial,
the vial wall and the absorbent head portion being configured to permit insertion of the collection stick into the vial through the open end so as to compress the absorbent head portion into contact with the closed end of the vial and thereby express the fluid sample from the absorbent head portion into the vial and to retain the absorbent head portion in a generally compressed state within the vial, without the cap sealing the open end of the vial, with the elongated handle portion being detached from the absorbent head portion.

2. The apparatus of claim 1 wherein the absorbent head portion comprises:
a support member detachably connected to the handle portion of the collection stick; and
an absorbent material operatively connected to the support member.

3. The apparatus of claim 2 further comprising a frangible member configured to detachably connect the support member to the handle portion of the collection stick.

4. The apparatus of claim 2 wherein the support member has a generally disk shape.

5. The apparatus of claim 1 wherein the vial has an inner diameter that decreases along at least a partial length of the vial in a direction from the open end toward the closed end of the vial.

6. The apparatus of claim 4 wherein the vial has an inner diameter that decreases along at least a partial length of the vial in a direction from the open end toward the closed end of the vial.

7. The apparatus of claim 6 wherein the disk has a diameter that is greater than an inner diameter of the vial generally proximate the closed end of the vial so as to create a frictional interference between the disk and the vial to permit detachment of the handle portion from the support member and retention of the absorbent head portion in the generally compressed state within the vial.

8. The apparatus of claim 1 further comprising a projection extending inwardly from the vial wall, the projection and the absorbent head portion being configured to permit insertion of the collection stick into the vial with the absorbent head portion traveling beyond the projection toward the closed end of the vial and being retained in the generally compressed state at a location between the closed end of the vial and the projection.

9. The apparatus of claim 8 wherein the projection comprises a radially inwardly directed rib.

10. The apparatus of claim 9 wherein the rib comprises a continuous annular rib.

11. The apparatus of claim 8 wherein the projection and the absorbent head portion are configured to provide at least one of a tactile and an audible indication when the absorbent head portion travels beyond the projection toward the closed end of the vial.

12. The apparatus of claim 2 wherein the support member includes at least one opening configured to permit the expressed fluid sample to migrate from one side of the support member to the opposite side.

13. The apparatus of claim 12 wherein the opening comprises a through-hole formed in the support member.

14. The apparatus of claim 12 wherein the opening comprises an indentation provided on a peripheral edge of the support member.

15. The apparatus of claim 1 further comprising a buffer solution contained within the vial.

16. The apparatus of claim 15 wherein the vial wall and the absorbent head portion are configured to permit insertion of the collection stick into the vial so as to compress the absorbent head portion against the closed end of the vial and thereby express the fluid sample from the absorbent head portion for mixture with the buffer solution and retain the absorbent head portion in the generally compressed state within the vial with the elongated handle portion being detached from the absorbent head portion.

17. The apparatus of claim 16 wherein the absorbent head portion comprises:
a support member detachably connected to the handle portion of the collection stick; and
an absorbent material operatively connected to the support member.

18. The apparatus of claim 17 wherein the support includes at least one opening configured to permit the mixture of the fluid sample and the buffer solution to migrate from one side of the support member to the opposite side.

19. The apparatus of claim 18 wherein the opening comprises a through-hole formed in the support member.

20. The apparatus of claim 18 wherein the opening comprises an indentation provided on a peripheral edge of the support member.

21. A method of collecting a fluid sample using a vial having a wall defining a closed end and an open end, a cap configured to selectively seal with the open end of the vial and a collection stick capable of collecting the fluid sample, the collection stick having an elongated handle portion and an absorbent head portion detachably connected to the handle portion, the method comprising:
absorbing the fluid sample with the absorbent head portion prior to insertion of the collection stick within the open end of the vial;
inserting the collection stick into the open end of the vial;
moving the collection stick toward the closed end of the vial to compress the absorbent head portion into contact with the closed end of the vial to thereby express the fluid sample from the absorbent head portion into the vial;
retaining the absorbent head portion in a generally compressed state within the vial without the cap sealing the open end of the vial;
detaching the handle portion from the absorbent head portion; and
removing the handle portion from the open end of the vial.

22. The method of claim 21 further comprising the step of selectively sealing the open end of the vial with the cap after the handle has been removed from the vial.

23. The method of claim 21 further comprising the steps of:
introducing a buffer solution within the vial; and
mixing the expressed fluid sample with buffer solution.

24. The method of claim 23 further comprising the step of selectively sealing the open end of the vial after the buffer solution has been introduced into the vial.

25. The method of claim 21 further comprising the step of providing at least one of a tactile and an audible indication during movement of the collection stick toward the closed end of the vial.

26. The method of claim 21 wherein the retaining step comprises frictionally engaging the absorbent head portion with the wall of the vial.

* * * * *